US012765830B2

(12) United States Patent
Baud et al.

(10) Patent No.: US 12,765,830 B2
(45) Date of Patent: Oct. 20, 2026

(54) CRANIODE

(71) Applicant: Wyss Center for Bio and Neuro Engineering, Geneva (CH)

(72) Inventors: Maxime Baud, Geneva (CH); Georgios Kouvas, Geneva (CH); Aleksander Sobolewski, Geneva (CH)

(73) Assignee: WYSS CENTER FOR BIO AND NEURO ENGINEERING, Geneva (CH)

(*) Notice: Subject to any disclaimer, the term of this patent is extended or adjusted under 35 U.S.C. 154(b) by 619 days.

(21) Appl. No.: 18/038,373

(22) PCT Filed: Nov. 18, 2021

(86) PCT No.: PCT/IB2021/060723
§ 371 (c)(1),
(2) Date: May 23, 2023

(87) PCT Pub. No.: WO2022/112908
PCT Pub. Date: Jun. 2, 2022

(65) Prior Publication Data

US 2023/0414157 A1 Dec. 28, 2023

Related U.S. Application Data

(60) Provisional application No. 63/117,712, filed on Nov. 24, 2020.

(51) Int. Cl.
*A61B 5/37* (2021.01)
*A61B 5/00* (2006.01)
(Continued)

(52) U.S. Cl.
CPC .............. *A61B 5/37* (2021.01); *A61B 5/0006* (2013.01); *A61B 5/0022* (2013.01);
(Continued)

(58) Field of Classification Search
None
See application file for complete search history.

(56) References Cited

U.S. PATENT DOCUMENTS 4,566,464 A 1/1986 Piccone et al.
4,735,208 A 4/1988 Wyler et al.
(Continued)

FOREIGN PATENT DOCUMENTS

EP 1303212 A1 4/2003
EP 2686059 A1 1/2014
(Continued)

OTHER PUBLICATIONS

International Search Report and Written Opinion for Int'l Application No. PCT/IB2021/060723, entitled "Craniode," consisting of 11 pages. Date of Mailing: Feb. 8, 2022.
(Continued)

*Primary Examiner* — Michael R Bloch
(74) *Attorney, Agent, or Firm* — Hamilton, Brook, Smith & Reynolds, P.C.

(57) ABSTRACT

A craniode is positioned in an intra-osseous fashion, namely partly or wholly within the bone of the skull, without penetrating the interior of the skull, while also being positioned below the scalp. A craniode can be used to sense electrical signals from a brain, to electrically stimulate the brain, to emit light signals to the brain, to detect light signals from the brain, to perform functional near infrared spectroscopy on the brain, and to perform photobiomodulation on the brain; and can, for example, provide the ability to perform these procedures in daily life. To resolve the problem of connectivity, each craniode can be connected, or can be equipped with features that make it connectable, to a subcutaneous cable, thus enabling the long-term usage of the craniode in real-life settings; or, active electrodes can be
(Continued)

used to transmit signals wirelessly. Transcutaneous and sub-scalp implantation techniques are also provided.

8 Claims, 10 Drawing Sheets

(51) Int. Cl.
*A61B 5/273* (2021.01)
*A61B 5/293* (2021.01)
*A61N 1/05* (2006.01)
*A61N 1/18* (2006.01)

(52) U.S. Cl.
CPC .......... *A61B 5/0031* (2013.01); *A61B 5/0075* (2013.01); *A61B 5/273* (2021.01); *A61B 5/293* (2021.01); *A61B 5/6847* (2013.01); *A61N 1/0539* (2013.01); *A61N 1/18* (2013.01); *A61B 2560/0406* (2013.01); *A61B 2560/0468* (2013.01); *A61B 2562/222* (2013.01); *A61B 2562/227* (2013.01)

(56) References Cited

U.S. PATENT DOCUMENTS 5,311,876 A 5/1994 Olsen et al.
5,562,670 A 10/1996 Per-Ingvar
5,857,978 A 1/1999 Hively et al.
5,995,868 A 11/1999 Osorio et al.
6,006,124 A 12/1999 Fischell et al.
6,016,449 A 1/2000 Fischell et al.
6,018,682 A 1/2000 Rise
6,044,304 A 3/2000 Baudino
6,061,593 A 5/2000 Fischell et al.
6,134,474 A 10/2000 Fischell et al.
6,201,980 B1 3/2001 Darrow et al.
6,354,299 B1 3/2002 Fischell et al.
6,466,822 B1 10/2002 Pless
6,473,639 B1 10/2002 Fischell et al.
6,549,804 B1 4/2003 Osorio et al.
6,560,486 B1 5/2003 Osorio et al.
6,594,524 B2 7/2003 Esteller et al.
6,597,953 B2 7/2003 Boling
6,597,954 B1 7/2003 Pless et al.
6,647,296 B2 11/2003 Fischell et al.
6,658,287 B1 12/2003 Litt et al.
6,726,678 B1 4/2004 Nelson et al.
6,810,285 B2 10/2004 Pless et al.
7,004,948 B1 2/2006 Pianca et al.
7,136,695 B2 11/2006 Pless et al.
7,174,206 B2 2/2007 Frei et al.
7,177,674 B2 2/2007 Echauz et al.
7,187,967 B2 3/2007 Kennedy
7,187,968 B2 3/2007 Wolf et al.
7,277,748 B2 10/2007 Wingeier et al.
7,302,298 B2 11/2007 Lowry et al.
7,421,297 B2 9/2008 Giftakis et al.
7,676,263 B2 3/2010 Harris et al.
7,787,945 B2 8/2010 Greene
7,930,035 B2 4/2011 Dilorenzo
8,036,736 B2 10/2011 Snyder et al.
8,057,519 B2 * 11/2011 Justis ................. A61B 17/7044 606/306
8,118,741 B2 2/2012 Beck-Nielsen
8,140,150 B2 3/2012 Greene
8,190,248 B2 5/2012 Besio et al.
8,224,434 B2 7/2012 Greene
8,396,557 B2 3/2013 Dilorenzo
8,543,199 B2 9/2013 Snyder et al.
8,628,472 B2 1/2014 Beck-Nielsen
8,718,777 B2 5/2014 Lowry et al.
8,849,368 B2 9/2014 Madsen et al.
8,884,767 B2 11/2014 Kidmose
9,044,188 B2 6/2015 Dilorenzo et al.
9,061,134 B2 6/2015 Askin et al.
9,113,801 B2 8/2015 Dilorenzo
9,155,861 B2 10/2015 Hetke et al.
9,232,903 B2 1/2016 Pless et al.
9,326,720 B2 5/2016 Mclaughlin
9,326,726 B2 5/2016 Lanning et al.
9,480,845 B2 11/2016 Harris et al.
9,622,675 B2 4/2017 Leyde et al.
9,649,049 B2 5/2017 Pless et al.
10,058,263 B2 8/2018 Negi et al.
10,413,208 B2 9/2019 Kidmose et al.
10,433,754 B2 10/2019 Nurmikko et al.
10,506,988 B2 12/2019 Karoly et al.
10,568,574 B2 2/2020 Williams et al.
2002/0138068 A1 9/2002 Watson et al.
2003/0004428 A1 1/2003 Pless et al.
2003/0028229 A1 2/2003 Rothman
2003/0074033 A1 4/2003 Pless et al.
2003/0144711 A1 7/2003 Pless et al.
2004/0054297 A1 3/2004 Wingeier et al.
2004/0092801 A1 5/2004 Drakulic
2004/0133119 A1 7/2004 Osorio et al.
2004/0138518 A1 7/2004 Rise et al.
2005/0075680 A1 4/2005 Lowry et al.
2006/0106430 A1 5/2006 Fowler et al.
2006/0111644 A1 5/2006 Guttag et al.
2006/0129056 A1 6/2006 Leuthardt et al.
2006/0287691 A1 12/2006 Drew
2006/0293723 A1 12/2006 Whitehurst et al.
2007/0016094 A1 1/2007 Pless
2007/0161919 A1 7/2007 Dilorenzo
2008/0027347 A1 1/2008 Harris et al.
2008/0027348 A1 1/2008 Harris et al.
2008/0027515 A1 1/2008 Harris et al.
2008/0091090 A1 4/2008 Guillory et al.
2008/0183097 A1 7/2008 Leyde et al.
2008/0312716 A1 * 12/2008 Russell ................ A61N 1/0539 607/45
2009/0088826 A1 4/2009 Bedenbaugh
2009/0112280 A1 * 4/2009 Wingeier ............... A61B 90/98 607/45
2009/0118804 A1 5/2009 Moffitt et al.
2009/0118806 A1 5/2009 Vetter et al.
2010/0145176 A1 6/2010 Himes
2010/0210964 A1 8/2010 Greene
2011/0166430 A1 7/2011 Harris et al.
2011/0172653 A1 7/2011 Schneider et al.
2012/0203079 A1 8/2012 Mclaughlin
2012/0302856 A1 11/2012 Chang et al.
2012/0302858 A1 11/2012 Kidmose et al.
2013/0085361 A1 4/2013 Mercanzini et al.
2013/0317575 A1 11/2013 Deisseroth et al.
2014/0094674 A1 4/2014 Nurmikko et al.
2015/0305643 A1 10/2015 Negi et al.
2015/0313497 A1 11/2015 Chang et al.
2016/0206236 A1 7/2016 Dilorenzo et al.
2017/0035316 A1 2/2017 Kuzniecky et al.
2017/0203111 A1 7/2017 Pless et al.
2017/0252568 A1 9/2017 Reed et al.
2017/0290521 A1 10/2017 Angle et al.
2017/0319092 A1 11/2017 Wendel-Mitoraj
2017/0319096 A1 11/2017 Kaiser et al.
2018/0055398 A1 3/2018 Westermann et al.
2018/0117331 A1 5/2018 Kuzniecky et al.
2018/0153474 A1 6/2018 Aeschlimann et al.
2018/0154152 A1 6/2018 Chabrol et al.
2018/0338765 A1 11/2018 Judy et al.
2019/0008403 A1 1/2019 Williams et al.
2019/0209007 A1 7/2019 D'Urso et al.
2019/0231204 A1 8/2019 Heydari et al.
2020/0022739 A1 * 1/2020 Benson ................ A61B 5/7275
2020/0038680 A1 2/2020 Degenaar et al.
2020/0078195 A1 3/2020 John et al.
2020/0187861 A1 6/2020 Williams et al.
2020/0330749 A1 * 10/2020 Gribetz .............. A61N 1/36085
2021/0013051 A1 1/2021 Tolosa et al.
2021/0267523 A1 9/2021 Donoghue et al.

(56) References Cited

U.S. PATENT DOCUMENTS

| | | | |
|---|---|---|---|
| 2021/0365117 | A1 | 11/2021 | Yoo et al. |
| 2025/0311954 | A1 | 10/2025 | Donoghue et al. |

FOREIGN PATENT DOCUMENTS

| | | | |
|---|---|---|---|
| WO | 00/25668 | A1 | 5/2000 |
| WO | 02/07596 | A1 | 1/2002 |
| WO | 2016/189216 | A1 | 12/2016 |
| WO | 2017/072769 | A1 | 5/2017 |
| WO | 2017/101977 | A1 | 6/2017 |
| WO | 2017/103380 | A1 | 6/2017 |
| WO | 2019/018879 | A1 | 1/2019 |
| WO | 2019/200918 | A1 | 10/2019 |
| WO | 2019/211314 | A1 | 11/2019 |
| WO | 2020/046532 | A1 | 3/2020 |
| WO | 2020/086473 | A1 | 4/2020 |
| WO | 2020/160613 | A1 | 8/2020 |

OTHER PUBLICATIONS

International Preliminary Report on Patentability for PCT/IB2021/060723, dated: May 30, 2023.

24/7 EEG SubQ, Specifications & Dimensions brochure, downloaded 2020.

Pal, D., et al., "A Genomics Revolution, Epilepsy Genetics and Precision Medicine," Epilepsy Professional, Epilepsy Action, 53:1-7 (Summer 2019).

Ranganatha Sitaram et al: "Closed-loop brain training: the science of neurofeedback"; Nature Reviews. Neuroscience,vol. 18, No. 2, Feb. 2017 (Feb. 2017), pp. 86-100, XP055604710, GB ISSN: 1471-003X, DOI: 10.1038/nrn.2016.164; abstract; figure 1.

Richardson, Mark., "Epilepsy today Rescued by First-Aid, Discover how Jane's friends and family made a difference when she needed first-aid," Epilepsy Action, Epilepsy today, (Sep. 2019).

UNEEG_Medical_Ultra Long-term EEG- a step towards seizure freedom Brochure, downloaded 2020.

Weisdorf, S., et al., "Ultra-long-term subcutaneous home monitoring of epilepsy-490 days of EEG from nine patients," Epilepsia, (Jul. 2019).

Ross et al. 1993. A percutaneous epidural screw electrode for intracranial electroencephalogram recordings. Neurosurgery 33(2):332-4.

Barnett et al. 1990. Epidural peg electrodes for the presurgical evaluation of intractable epilepsy. Neurosurgery 27(1):113-5.

* cited by examiner

CRANIODE

RELATED APPLICATION

This application is the U.S. National Stage of International Application No. PCT/IB2021/060723, filed on Nov. 18, 2021, which designates the U.S., published in English, and claims the benefit of U.S. Provisional Application No. 63/117,712, filed on Nov. 24, 2020. The entire teachings of the above applications are incorporated herein by reference.

BACKGROUND

Recording of electrical activity of the brain, such as in an electroencephalogram or EEG, is performed with electrodes, that is, electrically conductive elements placed either on or inside the head. If electrodes are placed on the head, the recording is called a scalp EEG. If the electrodes penetrate inside the brain, they are called intracerebral, or depth, electrodes. Various locations of electrodes for recording electrical activity of the brain, namely locations 1, 2, and 4-7 of FIG. 1, have been used. In locating the electrodes, it is generally the case that the closer the electrodes are to the brain, the higher the signal-to-noise ratio, but at the cost of increased invasiveness, and thus bleeding and infection risk, and typically decreased spatial coverage of neural tissue.

Scalp EEG, shown as location 1 in FIG. 1, is common in clinical practice. Sub-scalp EEG (location 2 in FIG. 1) comes in two variations: (i) simple 1-2 cm needles inserted into the scalp for in-patient recordings with cables connected directly to a bed-side amplifier, which is also common in clinical practice, and (ii) fully implanted long-term leads connected to an also implanted miniaturized recorder, which at present is only an emerging technology.

Epidural electrocorticography or ECoG (location 5 in FIG. 1) is common too, while subdural ECoG (location 6 in FIG. 1) is less common. Both are highly invasive procedures, typically requiring removal of a portion of the skull (craniotomy), and are thus limited to more severe cases requiring advanced diagnostics. Epidural ECoG (location 5 in FIG. 1) is less invasive than subdural ECoG, as it does not penetrate the dura mater, but yields somewhat worse signals. Transcranial ECoG screws or pegs (at location 4 in FIG. 1), which fully transfix the skull to touch the dura with no craniotomy, have been proposed, but did not find widespread clinical adoption. See References (1) and (2). One limitation of Transcranial ECoG electrodes is that each one of these small single-channel devices requires its own percutaneous interface (foreign body permanently exiting though the skin). Intracerebral recordings such as stereo-EEG (location 7 in FIG. 1), where needle-like electrodes are inserted through individual percutaneous interfaces and burr-holes into the parenchyma of the brain, are common clinical practice too.

In addition to recording brain signals, most of the planes of implantation illustrated in FIG. 1 are, or could be, used for brain stimulation. For example, stimulating the brain via scalp electrodes is commonly called tDCS or tACS (transcranial direct or alternating current stimulation) and its clinical use is currently an area of intensive research. Stimulating the brain though epidural electrodes is sometimes used to treat neuropathic pain, while intracerebral electrodes are used for deep brain stimulation (DBS) which is a treatment for Parkinson's disease and is being investigated for other neurological and psychiatric disorders.

Certain other recent modalities of interaction with the brain involve near infrared (or red) light. These include photobiomodulation of the brain, that is, therapeutic irradiation with near infrared (or red) light, e.g., for dementia, or functional near infrared spectroscopy. At present, both are done mainly with scalp mounted devices, which limit usability, especially long-term, and are less efficacious than they could be since much of the light does not reach the brain through the scalp and the skull.

SUMMARY

An intra-osseous device or craniode in accordance with an embodiment of the invention is positioned in an intra-osseous fashion, namely partly or wholly within the bone of the skull, without penetrating the interior surface of the skull, and while also being positioned wholly below the scalp, with no direct percutaneous interface, but rather connected to a subcutaneous cable or equipped with wireless transmission capabilities. A craniode can, for example, be used for one or more of: (i) to sense electrical signals from a brain, (ii) to electrically stimulate the brain, (iii) to emit light signals to the brain, (iv) to detect light signals scattered by the brain tissue, such as to perform functional near infrared spectroscopy on the brain, and (v) to perform photobiomodulation on the brain, and can provide the ability to perform these procedures in daily life. In one embodiment, to resolve the problem of connectivity, each craniode is equipped with features that make it connectable to a subcutaneous cable, such as for example a subcutaneous EEG lead, thus enabling the long-term usage of the craniode in real-life settings. In another embodiment, active electrodes are used to transmit or receive signals or energy wirelessly. Transcutaneous and sub-scalp implantation techniques are also provided.

In one embodiment according to the invention, an intra-osseous device is configured to at least one of sense electrical signals from a brain and electrically stimulate the brain. The device comprises an electrical conductor comprising an electrical contact surface configured to at least one of sense electrical signals from the brain and electrically stimulate the brain. At least a portion of a body of the device, comprising the electrical conductor, is configured to extend within a bone of a skull. The device comprises a size and a shape configured to be positioned wholly below a scalp and to extend at least partly within the bone of the skull without penetrating an interior of the bone of the skull.

In further, related embodiments, the intra-osseous device may comprise an electrical brain activity recording electrode, or an electrical brain stimulation electrode. The device may be electrically coupled to a sub-scalp cable, and may comprise an electrical attachment feature configured to electrically connect the electrical conductor to a sub-scalp cable. The device may comprise a wireless communications device configured to at least one of transmit and receive wireless signals, and the wireless communications device may be configured to transmit wireless signals to a data storage unit. The size and shape may comprise a diameter of the device of between about 0.5 millimeters and about 5 millimeters, and may comprise a height of the device of between about 2 millimeters and about 6 millimeters. The portion of the body of the device may comprise a threaded feature configured to secure the device within the bone of the skull, or may comprise a peg configured to extend within the bone of the skull. The electrical conductor may comprise a bottom electrical contact surface of the device configured to reside within the bone of the skull, and may extend within the device from the bottom electrical contact surface to a portion of the device that is configured to reside furthest from the brain. The device may further comprise an electrical isolation cap configured to electrically isolate the electrical attachment feature from tissue near the electrical attachment feature.

In further related embodiments, the electrical conductor may comprise a top portion, a bottom portion and a shaft portion extending between the top and bottom portions, the bottom portion defining the electrical contact surface; an electrically insulating material may be clad about the top portion and the shaft portion of the electrical conductor; the top portion of the electrical conductor may be configured to be positioned wholly below the scalp, said top portion configured to be electrically coupled to the sub-scalp cable; and the shaft portion and the bottom portion of the electrical conductor may be configured to be positioned into a hole extending into the bone of the skull, such that the electrical contact surface is positioned within the bone of the skull to sense brain activity from an intra-osseous space. The device may comprise a surgical metal bone screw, wherein the top portion of the electrical conductor is a head with cross-drive grooves, the shaft portion of the electrical conductor is threaded and is coated with the electrically insulating material, and the bottom portion is an uninsulated tip defining the electrical contact surface. The cross-drive head may be coated with the electrically insulating material except for an inner surface of the cross-drive grooves. The cross-drive grooves may be adapted to receive an electrical contact portion of the sub-scalp cable. The device may further comprise an isolating and protective cap adapted to mate with the cross-drive grooves not occupied by the sub-scalp cable to retain and isolate the sub-scalp cable therebetween. The electrical conductor may be removable from the device, while the device remains in the bone of the skull. The electrical conductor may comprise at least one of: stainless steel, titanium, MP35N, platinum, and platinum-iridium alloy. The device may further comprise an electrical insulator, which may comprise at least one of: a plastic, a ceramic, and an oxide. The electrical insulator may comprise at least one of: silicone, PEEK, PE, and LCP. The size and shape of the device may comprise a generally cylindrical shape, or may comprise a generally conical shape.

In another related embodiment that comprises the electrical attachment feature configured to electrically connect the electrical conductor to the sub-scalp cable, the electrical attachment feature may comprise an elastic flap under which a portion of the sub-scalp cable can be inserted to make electrical connection with the electrical conductor. The device may be formed of an elastic material, other than the electrical conductor.

In further related embodiments, the size and shape of the intra-osseous device may be configured to permit the device to fit entirely within the bone of the skull; or the size and shape may comprise a portion of the device configured to extend above a top surface of the bone of the skull, while remaining wholly underneath the scalp.

In another embodiment according to the invention, an intra-osseous device is configured to at least one of emit light signals to, and detect light signals from, the brain. The device comprises a light signal device configured to at least one of emit light signals to, and detect light signals from, a brain; at least a portion of a body of the device comprising at least one of a light emitter and a light detector being configured to extend within a bone of a skull; and the device comprising a size and a shape configured to be positioned wholly below a scalp and to extend at least partly within the bone of the skull without penetrating through to an interior of the bone of the skull.

In further related embodiments, the light signal device may be configured only to emit light signals to the brain; or may be configured only to detect light signals from the brain; or the light signal device may be configured both to emit light signals to, and detect light signals from, the brain. The light signal device may comprise a functional near infrared spectroscopy device, or may comprise a photobiomodulation device. The photobiomodulation device may comprise a photobiomodulation device configured to treat at least one of a neurological disorder and a neurodegenerative disorder. The device may be electrically coupled to a sub-scalp cable, and may comprise an electrical attachment feature configured to electrically connect the light signal device to a sub-scalp cable. The device may comprise a wireless communications device configured to at least one of transmit and receive wireless signals. The wireless communications device may be configured to at least one of transmit wireless signals to, and receive wireless signals from, a data storage unit. The size and shape may comprise a diameter of the device of between about 0.5 millimeters and about 5 millimeters, and may comprise a height of the device of between about 2 millimeters and about 6 millimeters. The portion of the body of the device may comprise a threaded feature configured to secure the device within the bone of the skull, or may comprises a peg configured to extend within the bone of the skull. The size and shape may be configured to permit the device to fit entirely within the bone of the skull, or the size and shape may comprise a portion of the device configured to extend above a top surface of the bone of the skull, while remaining wholly underneath the scalp.

Another embodiment according to the invention is a brain interface system. The system comprises any of the intra-osseous devices taught herein that comprise a sub-scalp cable; and the sub-scalp cable.

In further related embodiments, the brain interface system may further comprise an electrical signal processing device configured to at least one of communicate electrical signals to and from the intra-osseous device. The sub-scalp cable may comprise a tubular subcutaneous electroencephalogram lead. The sub-scalp cable may comprise electrical contacts to connect to at least one of a plurality of the intra-osseous devices. The brain interface system may comprise an electrical signal hub module configured to at least one of communicate electrical signals to and from the intra-osseous device, the electrical signal hub module being further configured to communicate with another device.

Another embodiment according to the invention is a brain interface system comprising any of the intra-osseous devices taught herein comprising a wireless communications device, and at least one of: (i) an electrical signal processing device configured to at least one of communicate electrical signals to and from the intra-osseous device; and (ii) an electrical signal hub module configured to at least one of communicate electrical signals to and from the intra-osseous device, the electrical signal hub module being further configured to communicate with another device.

Another embodiment according to the invention is a method of operating an intra-osseous device configured to at least one of sense electrical signals from a brain and electrically stimulate the brain. The method comprises, with an electrical contact surface of an electrical conductor of the intra-osseous device, performing at least one of: sensing electrical signals from the brain and electrically stimulating the brain; at least a portion of a body of the intra-osseous device, comprising the electrical conductor, extending within a bone of a skull during the at least one of the sensing of the electrical signals from the brain and the electrically stimulating the brain; and the at least one of the sensing of the electrical signals from the brain and the electrically stimulating the brain being performed while the intra-osseous device is positioned wholly below a scalp without penetrating through to an interior of the bone of the skull.

In further related embodiments, the method may comprise performing the at least one of the sensing electrical signals from the brain and the electrically stimulating the brain using any of the intra-osseous devices comprising an electrical contact surface taught herein. The method may comprise recording electrical brain activity using the intra-osseous device, or performing electrical brain stimulation using the intra-osseous device. Electrical signals may be transmitted to or from the intra-osseous device through a sub-scalp cable. A wireless signal may be transmitted from or received with the intra-osseous device, including by wirelessly transmitting to, or receiving from, a data storage unit. The method may comprise performing the at least one of the sensing of the electrical signals from the brain and the electrically stimulating the brain while the intra-osseous device is positioned entirely within the bone of the skull; or may comprise performing the at least one of the sensing of the electrical signals from the brain and the electrically stimulating the brain while a portion of the intra-osseous device extends above a top surface of the bone of the skull, and while remaining wholly underneath the scalp. With the intra-osseous device, electrical signals may be communicated at least one of to and from an electrical signal processing device; and may be communicated at least one of to and from an electrical signal hub module, the electrical signal hub module communicating with another device.

Another embodiment according to the invention is a method of operating an intra-osseous device configured to at least one of emit light signals to, and detect light signals from, a brain. The method comprises, with a light signal device of the intra-osseous device, performing at least one of: emitting light signals to, and detecting light signals from, the brain; at least a portion of a body of the intra-osseous device, comprising at least one of a light emitter and a light detector, extending within a bone of a skull during the at least one of the emitting light signals to, and detecting light signals from, the brain; and the at least one of the emitting light signals to, and detecting light signals from, the brain being performed while the intra-osseous device is positioned wholly below a scalp without penetrating through to an interior of the bone of the skull.

In further related embodiments, the method may comprise performing the at least one of the emitting light signals to, and detecting light signals from, the brain using any of the intra-osseous devices taught herein. The method may comprise performing functional near infrared spectroscopy using the intra-osseous device, or performing photobiomodulation using the intra-osseous device. The photobiomodulation may comprise treating at least one of a neurological disorder and a neurodegenerative disorder using the intra-osseous device. Electrical signals may be at least one of transmitted to and from the intra-osseous device through a sub-scalp cable, and wireless signals may be at least one of transmitted and received from the intra-osseous device. The method may comprise at least one of transmitting the wireless signal to, and receiving the wireless signals from, a data storage unit. The method may comprise performing the at least one of emitting light signals to, and detecting light signals from, the brain while the intra-osseous device is positioned entirely within the bone of the skull; or may comprise performing the at least one of emitting light signals to, and detecting light signals from, the brain while a portion of the intra-osseous device extends above a top surface of the bone of the skull, and while remaining wholly underneath the scalp. With the intra-osseous device, electrical signals may be at least one of communicated to and from an electrical signal processing device; and electrical signals may be at least one of communicated to and from an electrical signal hub module, the electrical signal hub module communicating with another device.

Another embodiment according to the invention is a method of installing an intra-osseous device to at least one of sense electrical signals from a brain, electrically stimulate the brain, emit light signals to the brain, and detect light signals from the brain. The method comprises: forming an opening in a scalp; forming an opening in a bone of a skull without penetrating through to an interior of the bone of the skull; inserting the intra-osseous device through the opening in the scalp into the opening in the bone of the skull without penetrating the interior of the bone of the skull; and closing the opening in the scalp such that the intra-osseous device is positioned wholly below the scalp and extending at least partly within the bone of the skull without penetrating the interior of the bone of the skull.

In further related embodiments, the opening in the bone of the skull may be underneath a site of the opening in the scalp; or the opening in the bone of the skull may be remote from the site of the opening in the scalp, the method comprising tunneling the intra-osseous device underneath the scalp to position the intra-osseous device into the opening in the bone of the skull remote from the site of the opening in the scalp. The method may comprise using a remotely actuated drill to install the intra-osseous device in the opening in the bone of the skull, the remotely actuated drill comprising an extension and a rotor mechanism to permit screwing of the intra-osseous device into the opening in the bone of the skull remote from the site of the opening in the scalp. The intra-osseous device may be electrically connected to a sub-scalp cable. A wireless communications device may be installed in the body in communication with the intra-osseous device. The method may comprise installing a data storage unit in the body. The method may further comprise installing an electrical signal processing device within the body to communicate electrical signals at least one of to and from the intra-osseous device. An electrical signal hub module may be installed within the body to at least one of communicate electrical signals to and from the intra-osseous device, and to communicate with a device external to the body. At least part of the intra-osseous device may be screwed into the opening in the bone of the skull. A peg-shaped portion of the intra-osseous device may be positioned into the opening in the bone of the skull. The method may comprise positioning the intra-osseous device entirely within the bone of the skull; or may comprise positioning a portion of the device to extend above a top surface of the bone of the skull, while remaining wholly underneath the scalp. The method may comprise installing any of the intra-osseous devices taught herein.

The intra-osseous devices, brain interface systems, and methods taught herein that include emission of light, detection of light, or both, may be used with light of a wavelength between about 380 nm and about 1400 nm, such as between about 380 nm and about 750 nm, for example between about 625 nm and about 750 nm, or between about 750 nm and about 1400 nm, or in more than one of the foregoing wavelength ranges, or in another range of the electromagnetic spectrum.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

An intra-osseous device or craniode in accordance with an embodiment of the invention is positioned in an intra-osseous fashion, namely partly or wholly within the bone of the skull, without penetrating the interior surface of the skull, and while also being positioned wholly below the scalp, with no direct percutaneous interface, but rather connected to a subcutaneous cable or equipped with wireless transmission capabilities. A craniode can, for example, be used for one or more of: (i) to sense electrical signals from a brain, (ii) to electrically stimulate the brain, (iii) to emit light signals (such as near infrared or red signals) to the brain, (iv) to detect light signals (such as near infrared signals) scattered by the brain tissue, such as to perform functional near infrared spectroscopy on the brain, and (v) to perform photobiomodulation on the brain, and can provide the ability to perform these procedures in daily life. In one embodiment, to resolve the problem of connectivity, each craniode is equipped with features that make it connectable to a subcutaneous cable, such as for example a subcutaneous EEG lead, thus enabling the long-term usage of the craniode in real-life settings. In another embodiment, active electrodes are used to transmit or receive signals or energy wirelessly. Transcutaneous and sub-scalp implantation techniques are also provided.

Figure 1:
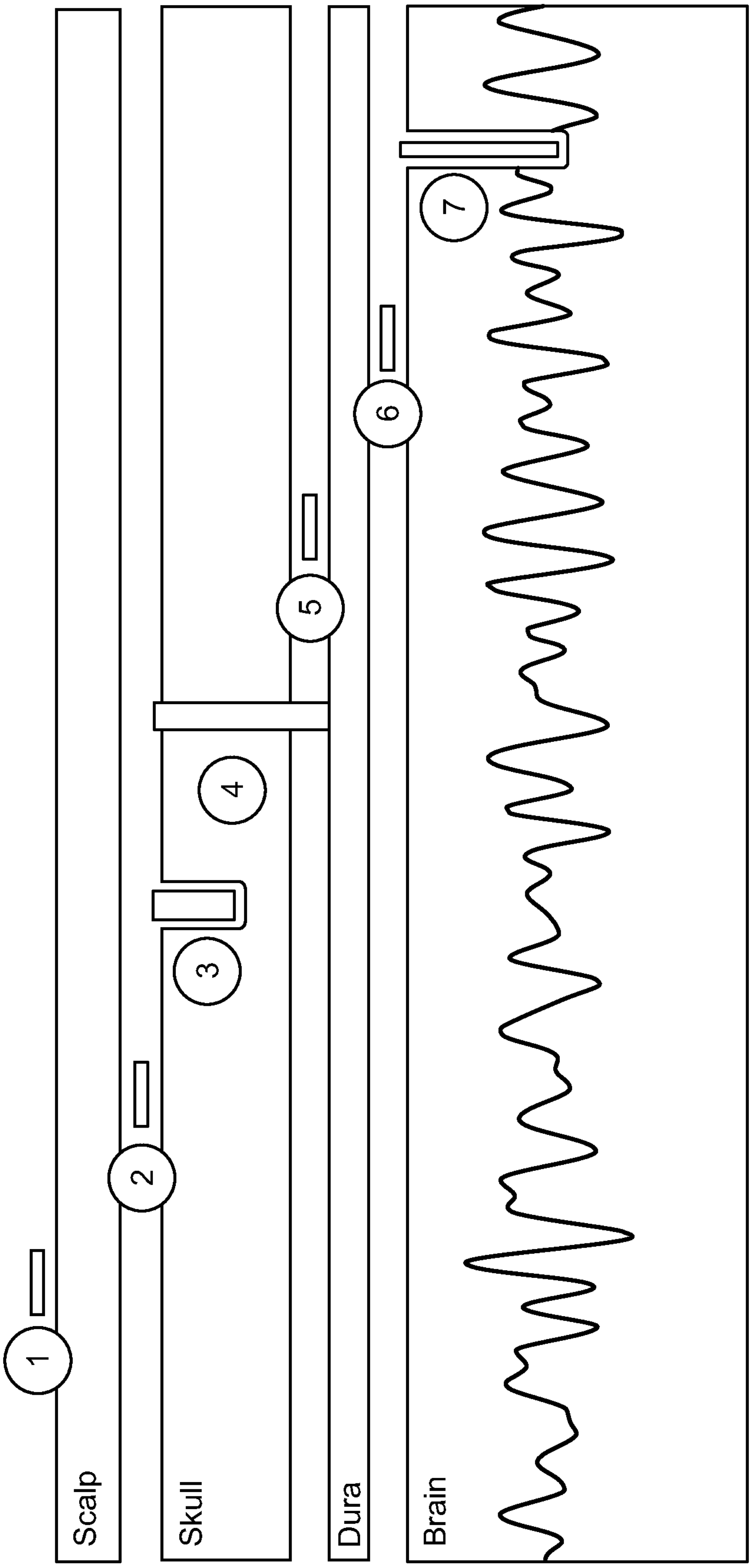
FIG. 1 is a schematic diagram of locations for placement of intra-osseous devices in accordance with an embodiment of the invention, as contrasted with locations in accordance with the prior art.

FIG. 1 is a schematic diagram of locations for placement of intra-osseous devices in accordance with an embodiment of the invention, for example as at location 3, as contrasted with locations in accordance with the prior art, as at locations 1, 2, and 4-7. Although referred to as a “craniode” herein, it will be appreciated that the intra-osseous devices herein include not only electrodes, but a variety of devices, including intra-osseous light-emitting and/or light detecting devices, as will be taught herein. As shown in FIG. 1, the intra-osseous device in accordance with an embodiment of the invention is positioned in an intra-osseous fashion, as shown at location 3, namely extending partly or wholly within the bone of the skull, without penetrating the interior of the skull, and while also being positioned wholly below the scalp. (Here, by extending “wholly” or “entirely” or “all” within the bone of the skull, it should be understood that the intra-osseous device may be considered as extending wholly or entirely or all within the bone of the skull when the intra-osseous device is located in an opening in the bone of the skull without protruding above an exterior surface of the skull, or penetrating an interior surface of the skull; but the intra-osseous device can have its top or other portion accessible through such an opening in the skull while still being considered as extending wholly or entirely or all within the skull). The intra-osseous positioning contrasts with the other locations shown, namely, the scalp location 1, the sub-scalp location 2, the transcranial location 4, the epidural location 5, the subdural location 6, and the intracerebral location 7. Each such previous technique of placement at locations 1, 2, and 4-7 suffers from their own drawbacks, such as poor signal-to-noise ratio for locations 1 and 2, and the potential for increased medical risks for locations 4-7.

Figure 2:
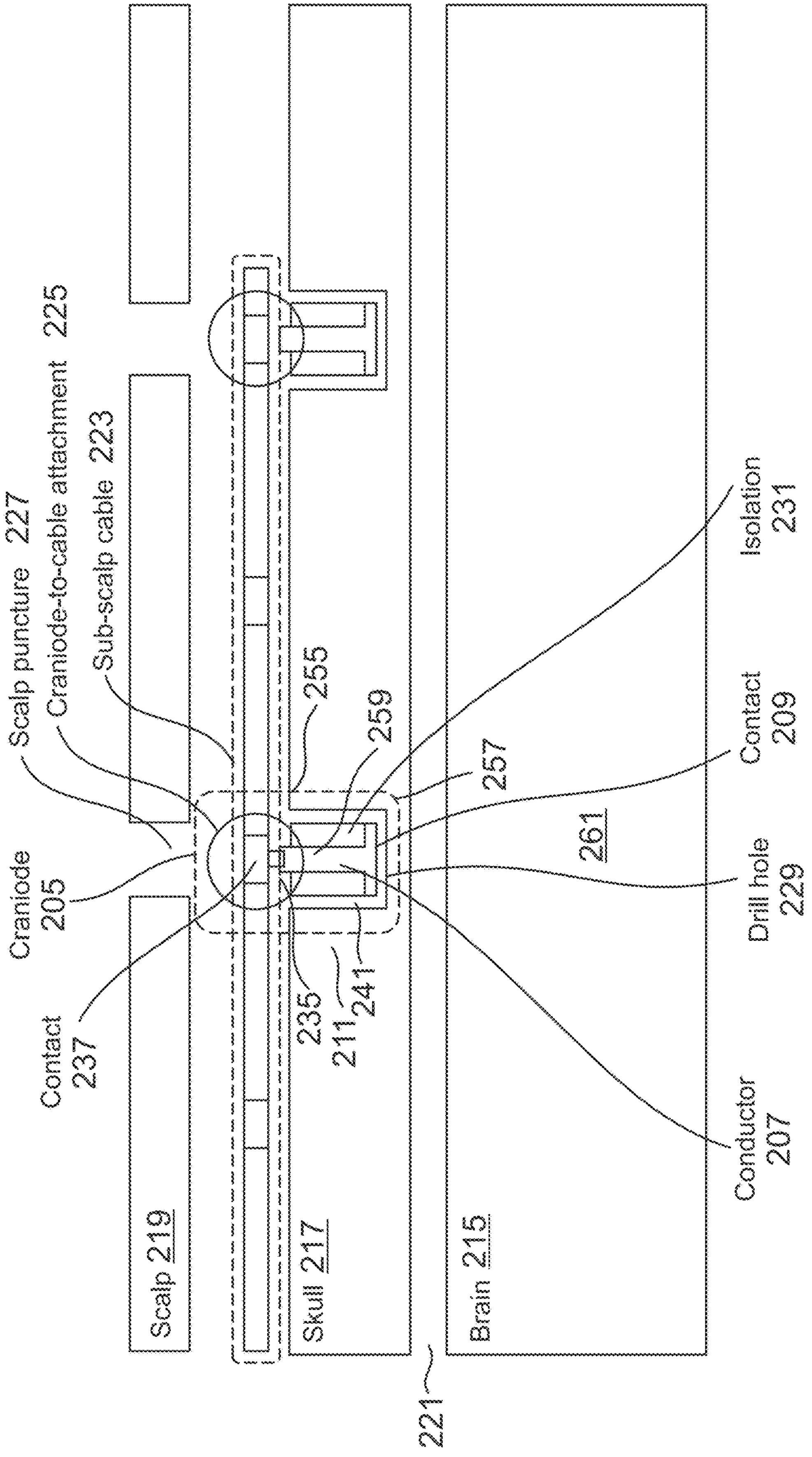
FIG. 2 is a schematic diagram illustrating an intra-osseous device or craniode in accordance with an embodiment of the invention.

FIG. 2 is a schematic diagram illustrating an intra-osseous device or craniode 205 in accordance with an embodiment of the invention. The intra-osseous device 205 can, for example, be configured to sense electrical signals from the brain 215, or to electrically stimulate the brain 215, or both. The intra-osseous device 205 comprises an electrical conductor 207 comprising an electrical contact surface 209 that can sense electrical signals from the brain 215, electrically stimulate the brain 215, or both. Part, or all, of the body 211 of the device 205, including the electrical conductor 207, extends within a bone of the skull 217. At least part of the electrical conductor 207 can be clad in an insulator, so that it is not in electrical contact with the bone. The intra-osseous device 205 has a size and a shape so that the device can be positioned wholly below the scalp 219, while also extending at least partly within the bone of the skull 217, and without penetrating through to an interior 221 of the bone of the skull 217. For example, the size and shape of the intra-osseous device 205 can include that the maximum dimension of the intra-osseous device 205, when implanted in its operative position at least partly in the skull 217 and without penetrating the interior 221 of the bone of the skull 217, is small enough that the intra-osseous device 205 can remain wholly below the scalp 219. The intra-osseous device 205 can be electrically coupled to a sub-scalp cable 223. In some embodiments, the intra-osseous device 205 can be permanently attached to a sub-scalp cable 223. For example, the sub-scalp cable 223 can be laser welded to the intra-osseous device 205, and the assembly overmolded with an insulator, such as silicone. Alternatively, the intra-osseous device 205 can be not permanently attached to the sub-scalp cable 223. The intra-osseous device 205 can comprise an electrical attachment feature 225 configured to electrically connect the electrical conductor 207 to the sub-scalp cable 223. Such an electrical attachment feature 225 can, for example, permit the intra-osseous device 205 to be coupled and de-coupled from the sub-scalp cable 223.

In the example of FIG. 2, the intra-osseous device or craniode 205 is an electrical brain activity recording electrode (sensor), but it will be appreciated that one or more similar features to those shown in FIG. 2, such as the placement of the craniode 205 and its electrical connections, can be used for other devices taught herein. For example, the craniode 205 can be an electrical brain stimulation electrode. In FIG. 2, the craniode 205 is placed through a puncture 227 in the scalp 219 in a bespoke hole 229 drilled, or otherwise made, in the skull 217. The hole 229 does not go all the way through the skull 217. Thus, it can be said that the craniode 205 records an "intraosteal" EEG, or performs other intraosteal functions in other examples taught herein. The main body 211 of the craniode 205 can, for example, be generally cylindrical or generally conical in shape. The size and shape of the craniode 205 can, for example, be a diameter between about 1 mm and about 5 mm and a height between about 2 mm and about 6 mm, although it will be appreciated that other dimensions can be used. The craniode 205 can have a threaded feature 339 (see FIG. 3) to secure it in the skull 217, making it a screw, or not, making it a peg 241 (as in FIG. 2); it can also have other features to secure it to the bone. Where pegs are referred to herein, a peg can include other features to facilitate anchoring in the bone, such as barbs, nubs, or similar small surface features to facilitate better anchoring in the bone. Although the craniode 205 at least partly or wholly extends within the skull, it need not, however, necessarily be "secured" to the skull 217, as for example occurs when it is screwed into the skull; instead, it can, for example, merely extend within the opening 229 in the skull 217 without necessarily being secured to the bone, as can occur with a peg shape for the body 211 of the craniode 205.

In FIG. 2, the bottom portion 209 of the craniode is electrically conductive, making it a sensing surface of the craniode, or its electrical contact surface 209. Most or all of the side walls of the craniode are electrically isolating 231, with an electrical conductor 207 extending inside the craniode 205 from the electrical contact surface 209 to the part of the craniode that is furthest from the brain 215. For better signal-to-noise ratio, the craniode 205 can be further equipped with a feature, such as a silicone cap 333 (see FIG. 3), designed to electrically isolate the electrical connection 235 from surrounding tissue, such as muscle that produces electromyographic signals. At the top of the craniode 205 there is the electrical attachment feature 225 allowing attachment of the craniode 205 to the isolated sub-scalp cable 223, so that an electrical connection 235 is formed between the sub-scalp cable's contact 237 and the craniode's conductor 207. The EEG signals registered by the craniode's electrical contact surface 209 propagate down the sub-scalp cable 223 to an implantable acquisition device (such as data storage unit 769 in FIG. 7). In another example, electrical stimulation signals can propagate down the sub-scalp cable 223 to be provided to the craniode's conductor 207 so that the electrical contact surface 209 provides electrical stimulation to the brain 215. The sub-scalp cable 223 can, for example, be a tubular subcutaneous EEG lead, with multiple cylindrical contacts 237, any of which can be attached to craniodes 205. The conductive parts of the craniode 205, such as the electrical conductor 207, can for example be manufactured with a conductive metallic material that is biocompatible, or combinations of such materials, for example: stainless steel, titanium, MP35N, platinum or Platinum-Iridium alloy. The insulating parts of the craniode 205, such as electrical insulator 231, can for example be manufactured with an isolating material that is biocompatible, or combinations of such materials, such as, for example: silicone, PEEK, PE, LCP or other plastics, ceramics, oxides, or thin firm depositions of isolating materials.

In one example, the electrical conductor 207 can be removable from the intra-osseous device 205, while the device 205 remains in the bone of the skull 217. That is, the electrical conductor 207 can be a component that can be separated from the rest of the device 205, for example, by being unscrewed or untapped. In that way, the electrical conductor 207 can be replaced with a bone mimicking material when it is not needed for recording anymore.

In the embodiment of FIG. 2, the electrical conductor 207 includes a top portion 255, a bottom portion 257 and a shaft portion 259 extending between the top portion 255 and bottom portion 257. The bottom portion 257 defines the electrical contact surface 209. An electrically insulating material 231 is clad about the top portion 255 and the shaft portion 259 of the electrical conductor 207. The top portion 255 of the electrical conductor 207 is configured to be positioned wholly below the scalp 219. The top portion 255 can be configured to be electrically coupled to a sub-scalp cable, for example by a permanent attachment or by including the electrical attachment feature 225 configured to receive a portion of the sub-scalp cable 223. The shaft portion 259 and the bottom portion 257 of the electrical conductor 207 are configured to be positioned into the hole 229 extending into the bone of the skull 217, such that the electrical contact surface 209 is positioned within the bone of the skull 217 to sense brain activity from the intra-osseous space 261.

It will be appreciated that, while one intra-osseous device 205 is shown in FIG. 2, embodiments can include multiple intra-osseous devices 205 being attached to the sub-scalp cable 223, for example using electrical attachment features 225. In another embodiment, one or more craniode devices 205 can be permanently attached to the sub-scalp cable 223, possibly making the tunneling of the connecting sub-scalp cable 223 more challenging, but negating the need for the electrical attachment features 225. The sub-scalp cable 223 itself can then have a connector to a recording implant (such as data storage unit 769 in FIG. 7).

Figure 3:
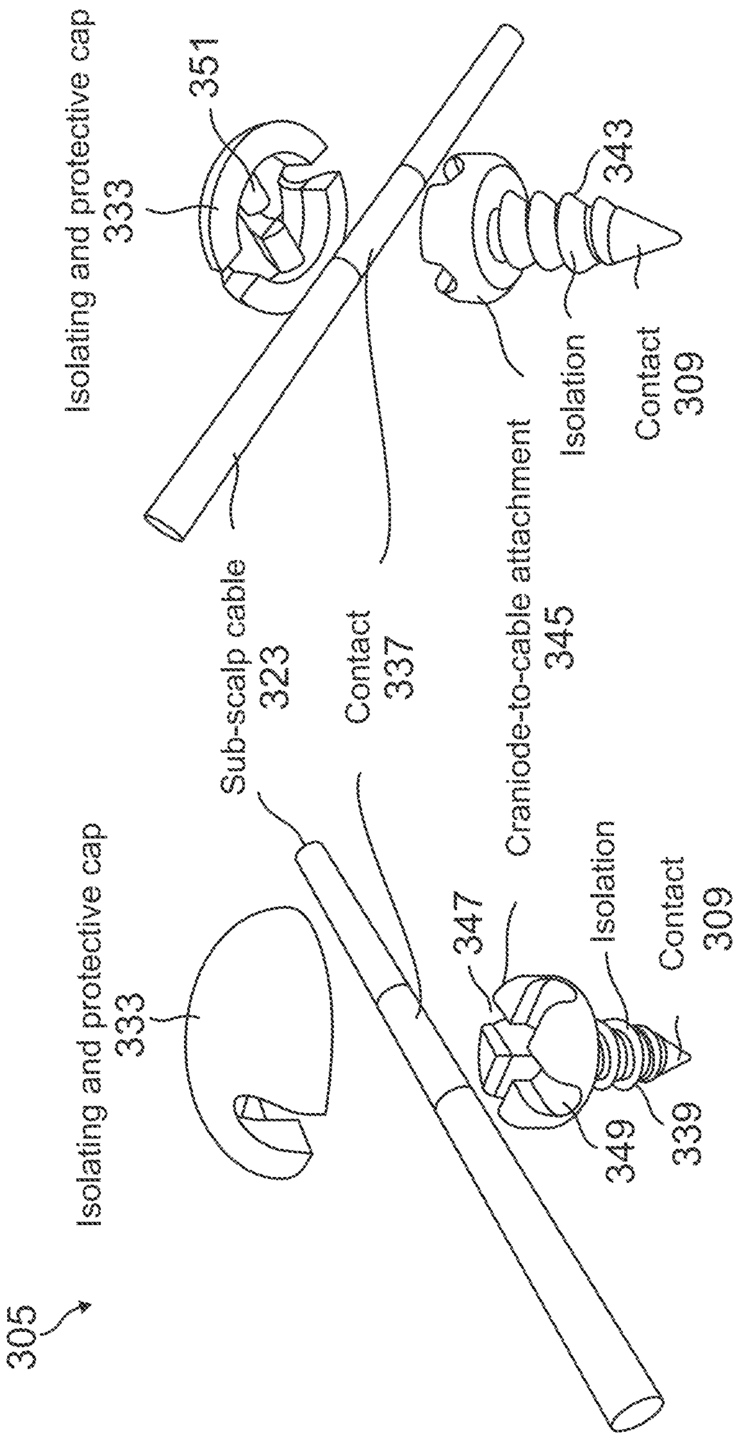
FIG. 3 is a schematic diagram of an intra-osseous device having a threaded feature to secure it to the bone of the skull, and a cross-drive electrical connection, in accordance with an embodiment of the invention.

FIG. 3 is a schematic diagram of an intra-osseous device 305 having a threaded feature 339 to secure it to the bone of the skull, and a cross-drive electrical connection, in accordance with an embodiment of the invention. In FIG. 3, the intra-osseous device 305 includes a surgical metal bone screw 343, where the top portion of the electrical conductor is a head 345 with cross-drive grooves 347, the shaft portion of the electrical conductor is the threaded attachment feature 339, and is coated with electrically insulating material, and the bottom portion is an uninsulated tip defining the electrical contact surface 309. The cross-drive head 345 can be coated with the electrically insulating material except for an inner surface 349 of the cross-drive grooves 347. The cross-drive grooves 347 can be adapted to receive an electrical contact portion 337 of the sub-scalp cable 323. The device 305 can further include an isolating and protective cap 333 adapted to mate with the cross-drive grooves 347 not occupied by the sub-scalp cable 323 to retain and isolate the sub-scalp cable 323 therebetween. For example, the cap 333 can include mating features 351 that fit into the cross-drive grooves 347 not occupied by the sub-scalp cable 323.

In the example of FIG. 3, the craniode 305 is a surgical metal bone screw 343 with a cross-drive. Its threaded portion 339 is coated with a thin layer of isolating material, with the uninsulated tip of the screw forming the contact 309. The head 345 of the screw is also coated with insulation, except the inner aspects 349 of the cross-drive grooves

347. The cross-drive grooves 347 can be used to screw the craniode 305 into the skull, but also double as the craniode-to-cable attachment. The bottom of the grooves 349 can be semicircular in cross-section, with a diameter closely matching the diameter of the sub-scalp cable 323. Thus, the cable contact 337 can be trapped by one of the grooves, when aligned by the surgeon with the sub-scalp cable 323. The other groove then serves to attach the silicone isolating and protective cap 333.

Figure 4:
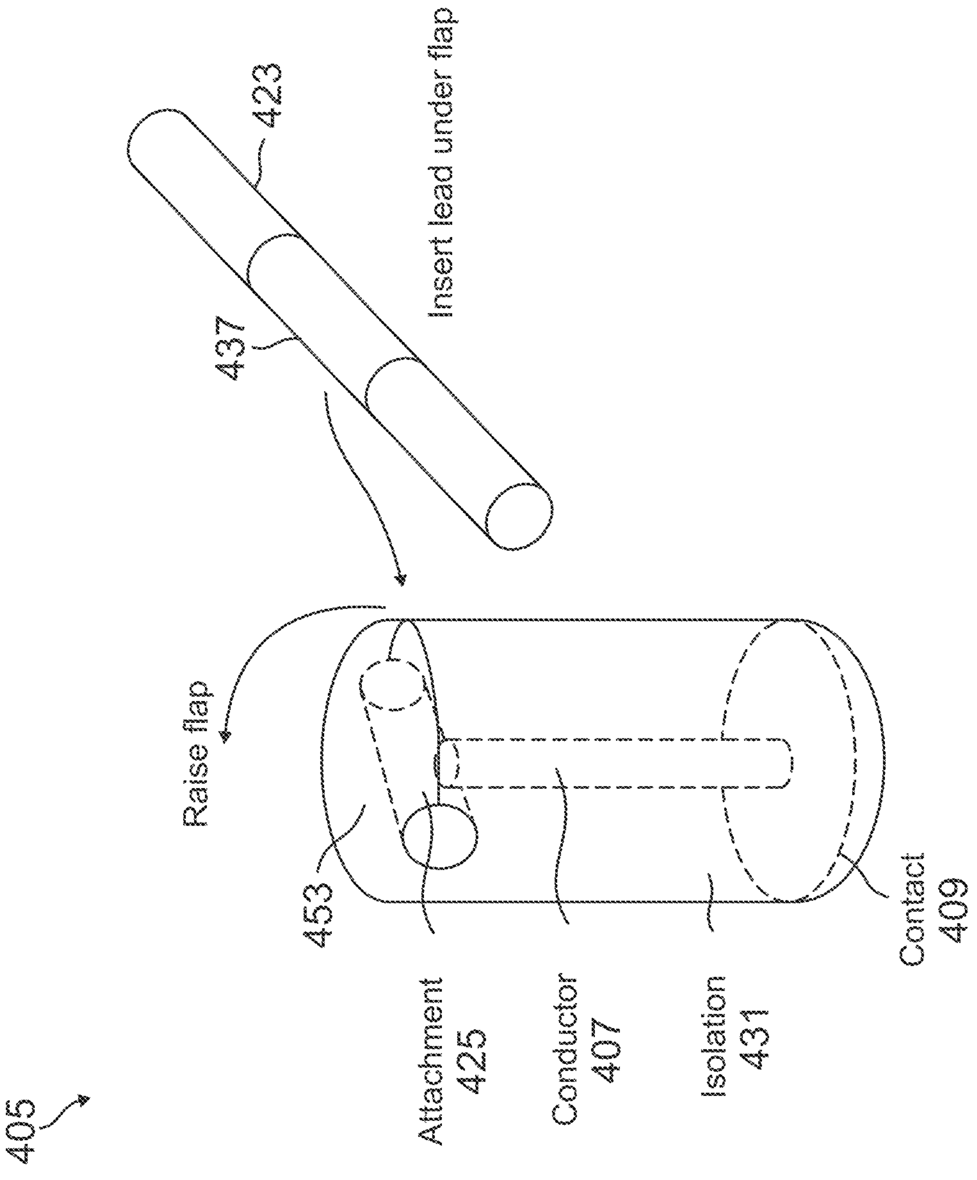
FIG. 4 is a schematic diagram illustrating another embodiment of an intra-osseous device, including an elastic flap, in accordance with an embodiment of the invention.

FIG. 4 is a schematic diagram illustrating another embodiment of an intra-osseous device 405, including an elastic flap 453, in accordance with an embodiment of the invention. Here, an electrical attachment feature 425 allows the electrical conductor 407 to be connected to the sub-scalp cable 423. The electrical attachment feature 425 includes the elastic flap 453, which is raised in on order to permit insertion of a portion of the sub-scalp cable 423 under the elastic flap 453, so that the electrical contact 437 of the sub-scalp cable 423 forms an electrical connection with the electrical conductor 407. The device 405 can, for example, be formed of the elastic material, such as a plastic, other than the electrical conductor 407. The elastic material can function as an electrical insulator 431, while the bottom surface of the electrical conductor functions as the electrical contact surface 409.

Figure 5:
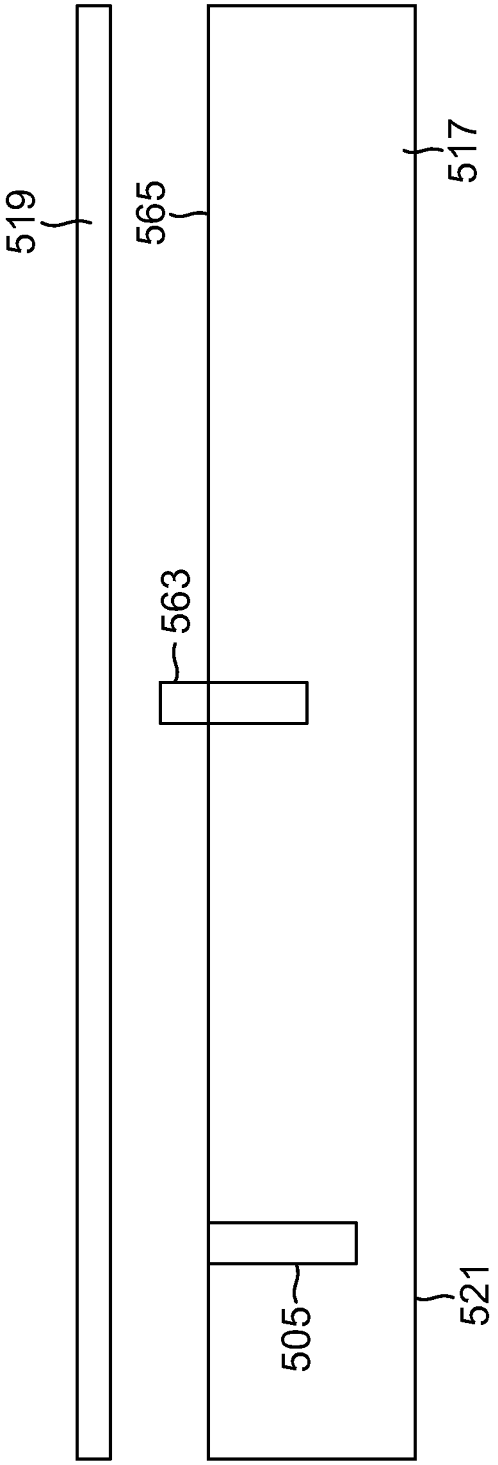
FIG. 5 is a schematic diagram illustrating positioning of an intra-osseous device entirely within, and partly within, the skull, in accordance with embodiments of the invention.

FIG. 5 is a schematic diagram illustrating positioning of an intra-osseous device 505 entirely within, and partly within, the skull, in accordance with embodiments of the invention. In one embodiment, shown on the left of FIG. 5, the size and shape of the intra-osseous device 505 is configured to permit the device 505 to fit entirely within the bone of the skull 517. In another embodiment, the size and shape of the intra-osseous device 505 is such that a portion 563 of the device is configured to extend above a top surface 565 of the bone of the skull 517, while remaining wholly underneath the scalp 519, and without penetrating the interior 521 of the skull 517.

Figure 6:
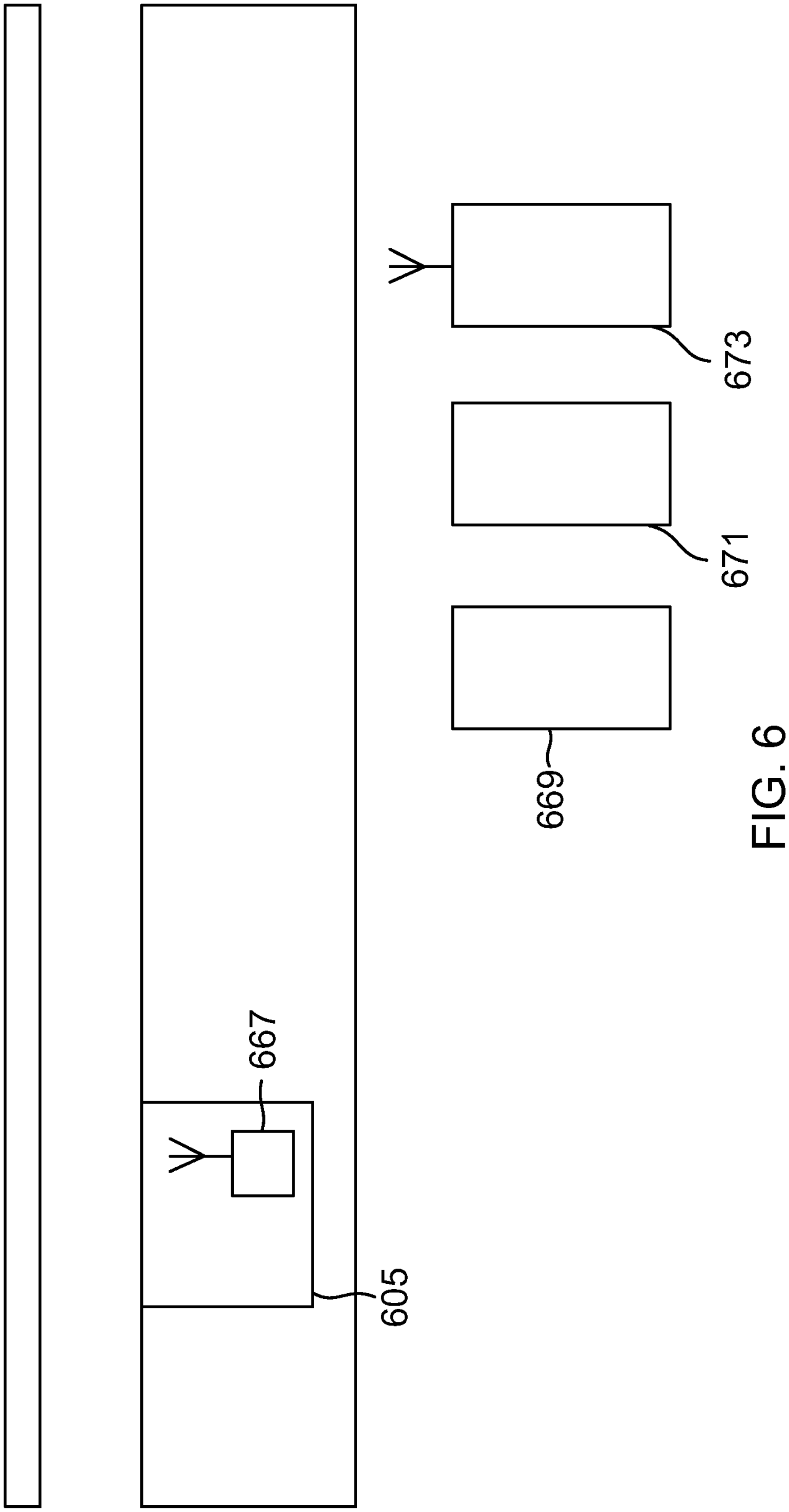
FIG. 6 is a schematic diagram illustrating use of wireless communications with an intra-osseous device, in accordance with an embodiment of the invention.

FIG. 6 is a schematic diagram illustrating use of wireless communications with an intra-osseous device 605, in accordance with an embodiment of the invention. Here, the intra-osseous device 605 includes a wireless communications device 667, which can transmit wireless signals from the intra-osseous device 605, receive wireless signals transmitted wirelessly from another device to the intra-osseous device 605, or both. The wireless communications device 667 can, for example, communicate using any of a variety of different possible wireless communications protocols and frequency bands, such as those that permit interoperability of medical device networks, such as Wi-Fi (wireless network), Bluetooth®, Wireless Medical Telemetry Service (WMTS) or others. As some examples, the wireless communications device 667 can transmit data in frequency bands such as 608-614 MHz, 902-928 MHz, 1395-1400 MHz, 1427-1432 MHz, or 2.4-2.5 GHz, for example using an IEEE® 802.11 or Bluetooth® radio. In one embodiment, the wireless communications device 667 is configured to transmit wireless signals to a data storage unit 669, which can be positioned within a body, or external to a body. For example, the intra-osseous device 605 can be an "active" electrode that pre-amplifies its sensed brain signal and transmits it to a data-storage unit 669 via a wireless connection. In one example, the data storage unit 669 can be in an implant, such as a cochlear implant, positioned within the body. In another embodiment, the intra-osseous device 605 can be part of a brain interface system, which can, for example, include any of the intra-osseous devices taught herein and can include a wireless communications device 667. For example, as shown in FIG. 6, the brain interface system can include the intra-osseous device 605 with its wireless communications device 667, which can communicate signals with an electrical signal processing device 671 (which can include a microprocessor) implanted within a body, or external to a body. The brain interface system can also include an electrical signal hub module 673 configured to be implanted within a body, or external to a body, which can communicate electrical signals to and from the intra-osseous device 605. The electrical signal hub module 673 can be further configured to communicate with another device within the body, or external to the body, for example a data storage unit, a networking or communications component, or a signal processing device.

Figure 7:
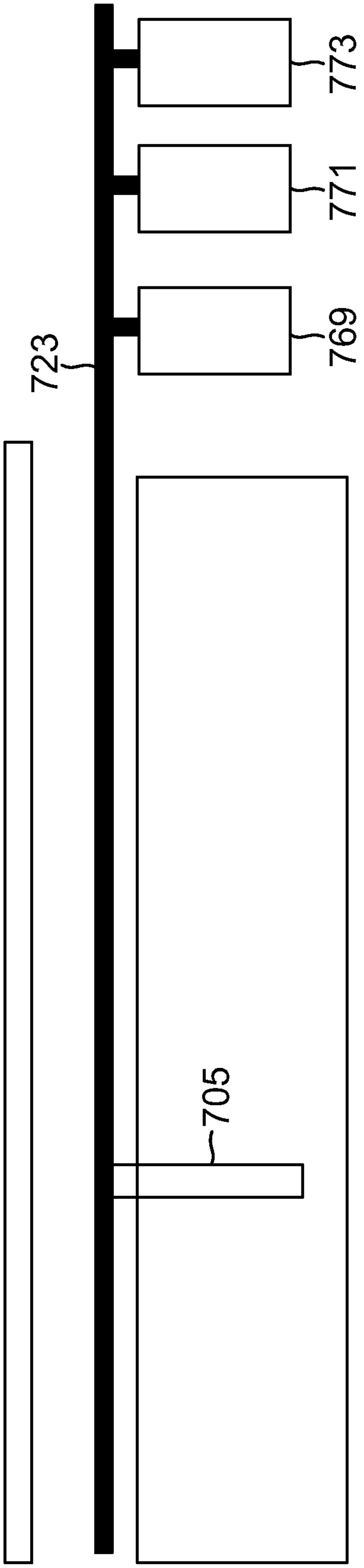
FIG. 7 is a schematic diagram illustrating use of wired or cabled communications with an intra-osseous device, in accordance with an embodiment of the invention.

FIG. 7 is a schematic diagram illustrating use of wired or cabled communications with an intra-osseous device 705, in accordance with an embodiment of the invention. In this embodiment, some or all of the communications between devices is performed using wires or cables, as opposed to wireless communications. For example, the brain interface system in FIG. 7 can include a sub-scalp cable 723. Signals can be communicated along the sub-scalp cable 723 to and from a data storage unit 769, which can be positioned within the body. In addition, the brain interface system can include an electrical signal processing device 771 (which can include a microprocessor) configured to be implanted within a body, and configured to at least one of communicate electrical signals to and from the intra-osseous device 705. The sub-scalp cable 723 can, for example, include a tubular subcutaneous electroencephalogram lead, and can include electrical contacts to connect to one or more of the intra-osseous devices 705. The brain interface system can also include an electrical signal hub module 773 configured to be implanted within a body, which can communicate electrical signals to and from the intra-osseous device 705. The electrical signal hub module 773 can be further configured to communicate with a device external to the body.

Various different possible methods can be used to install an intra-osseous device in the body, in accordance with embodiments of the invention. In one technique, described with reference to FIG. 2, first a puncture hole 227 is made in the scalp 219 to enter the sub-scalp plane. This opening 227 can be of varied length, from a millimetric puncture to a centimetric incision, depending on the implantation technique used on top of the final location of each craniode. A hole 229 of a corresponding diameter and depth is then drilled into the skull. The craniode or other intra-osseous device 205 is then screwed or pushed into the skull. Subsequently, the craniode is attached to the sub-scalp cable 223, for example using the electrical attachment features 225. The sub-scalp cable 223 can be routed under the skin either prior to placement of the craniodes 205, or after, or the two procedures can be done intermittently: first craniode puncture holes 227 are made, then the sub-scalp cable 223 is routed utilizing the puncture holes 227, then craniodes 205 are implanted and connected to the sub-scalp cable 223.

In one embodiment, implantation of craniodes or other intra-osseous devices taught herein can be permanent, due to bone remodeling. The indication for the implantation can thus be patients with brain disorders in need of chronic EEG monitoring.

In another embodiment, a method of installing an intra-osseous device can be as follows. The intra-osseous device can be used to perform one or more of: sensing electrical signals from a brain, electrically stimulating the brain, emitting light signals (such as near infrared or red signals) to the brain, and detecting light signals (such as near infrared signals) from the brain. With reference to FIG. 2, the method comprises: forming an opening 227 in a scalp 219; forming an opening 229 in a bone of a skull without penetrating through to an interior 221 of the bone of the skull 217; inserting the intra-osseous device 205 through the opening 227 in the scalp 219 into the opening 229 in the bone of the skull without penetrating the interior 221 of the bone of the skull; and closing the opening 227 in the scalp such that the intra-osseous device 205 is positioned wholly below the scalp 219 and extending at least partly within the bone of the skull 217 without penetrating the interior 221 of the bone of the skull. The opening 229 in the bone of the skull 217 can be underneath the site of the opening 227 in the scalp, as shown in FIG. 2. Having the intra-osseous device 205 inserted in the bone via a puncture hole 227 through the skin directly above the insertion site 229, as in FIG. 2, has the advantage of close controllability on the insertion target and applying forces perpendicular to the skull. A disadvantage of the technique is a potential higher infection risk because the skin has been breached just above the inserted material, and there has to be one incision for each craniode.

Figure 8:
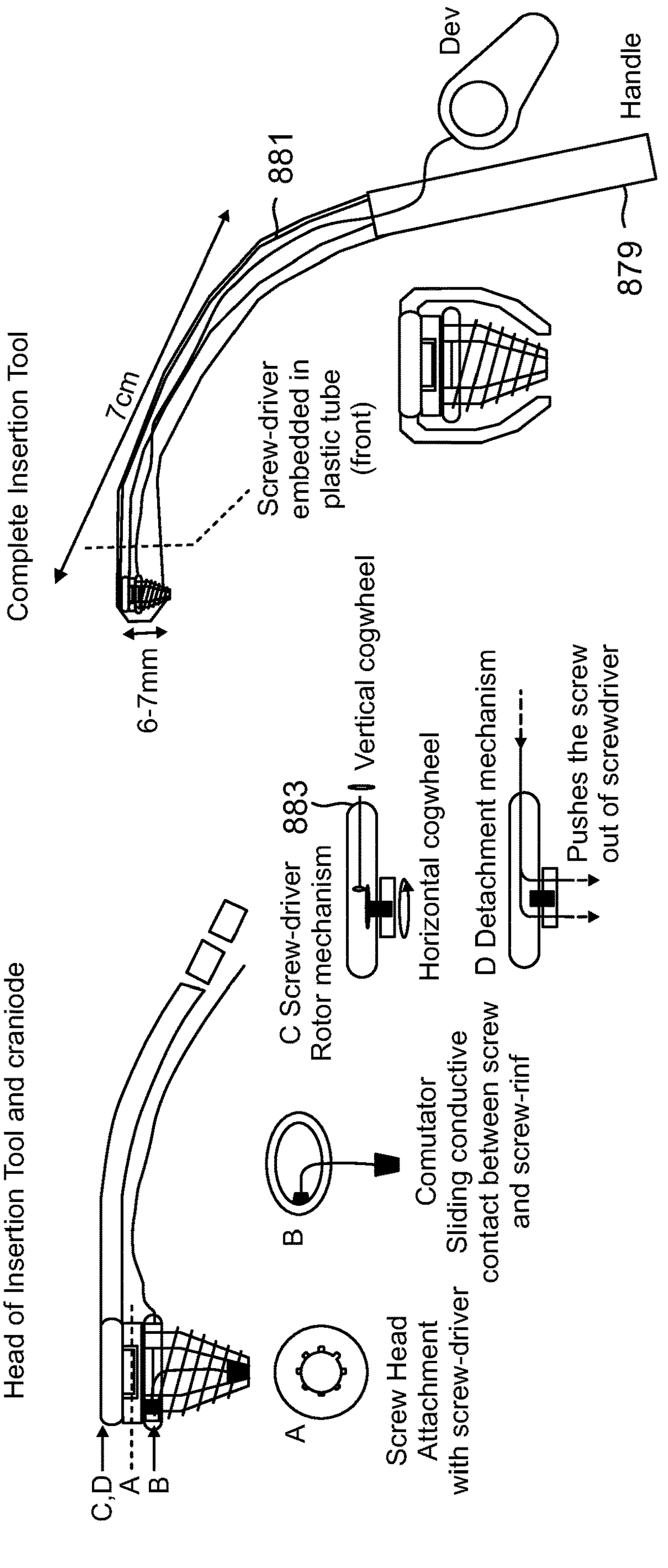
FIGS. 8 and 9 are schematic diagrams illustrating a method and tool for implanting an intra-osseous device, where an opening for the intra-osseous device in the bone of the skull is remote from the site of an opening in the scalp.
Figure 9:
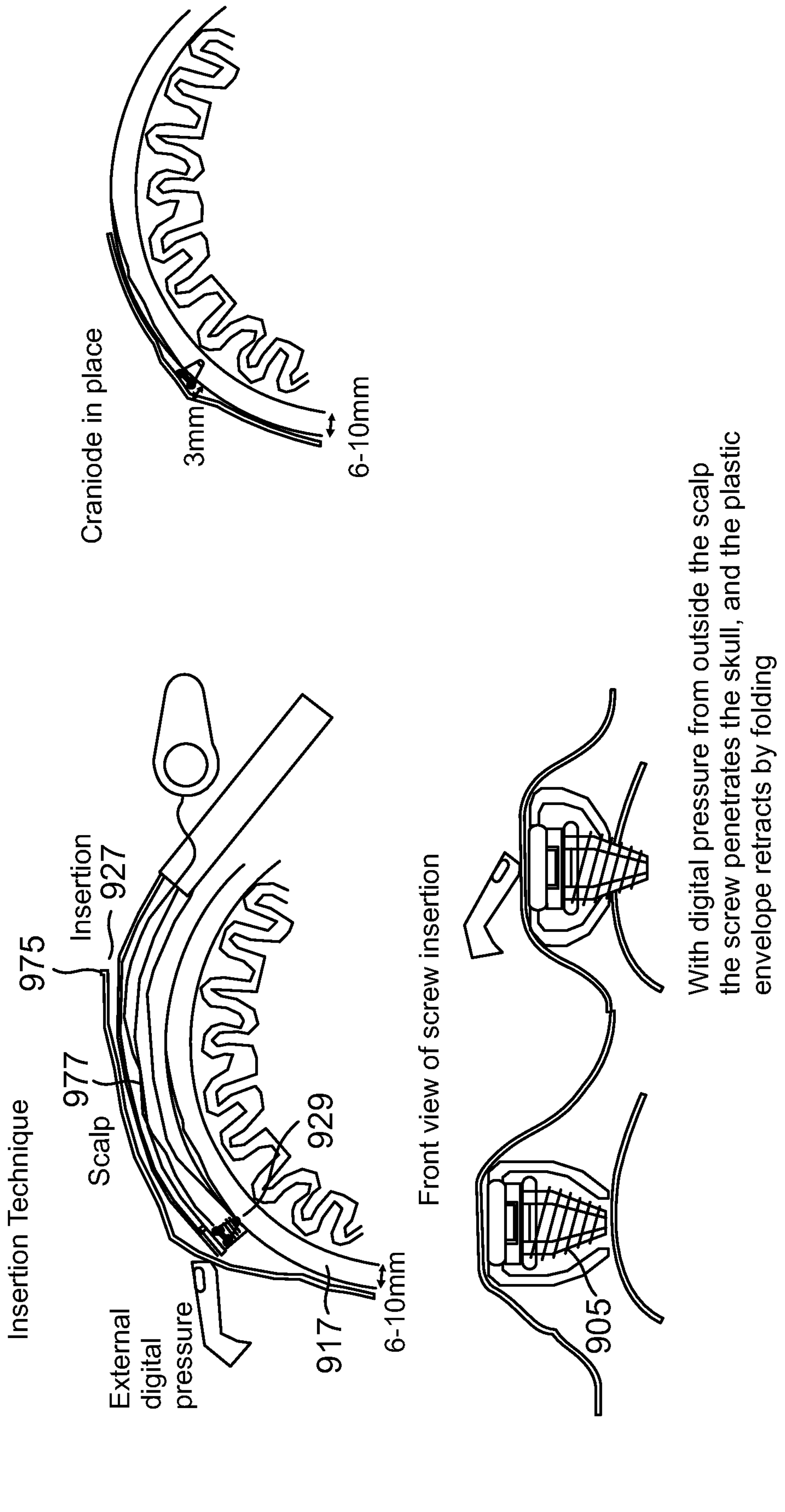

In another embodiment, illustrated in FIGS. 8 and 9, each intra-osseous device 905 (see FIG. 9) is inserted in the bone by first being inserted through a skin incision 975 at a distance, and then being tunneled 977 in the sub-scalp plane. Specific sub-scalp tools, such as those shown in FIGS. 8 and 9, can be used for that purpose. The advantage of this technique is that the skin is intact above the inserted material, that is, above the device 905, thereby minimizing the risk of device infection. In addition, potentially many intra-osseous devices 905 can be implanted via one remote incision 975.

In the method of FIGS. 8 and 9, the opening 929 (see FIG. 9) in the bone of the skull is remote from the site of the opening 927 in the scalp. The method includes tunneling 977 the intra-osseous device underneath the scalp 919 to position the intra-osseous device 905 into the opening 929 in the bone of the skull 917 remote from the site of the opening 927 in the scalp. The method can include using a remotely actuated drill 879 (see FIG. 8) to install the intra-osseous device in the opening in the bone of the skull. The remotely actuated drill 879 can include an extension 881 and a rotor mechanism 883 to permit screwing of the intra-osseous device into the opening in the bone of the skull remote from the site of the opening in the scalp. The drill 879 can function as a drilling and screwing tool, and to enable navigation in the sub-scalp space. As shown in panel A in FIG. 8, the intra-osseous device can have a screw head attachment with the screw-driver portion of the tool 879. In panel B, a commutator can permit sliding conductive contact between the screw and the screw ring. In panel C, there is shown the screw-driver rotor mechanism, which can for example feature a vertical cogwheel and a horizontal cogwheel. In panel D, a detachment mechanism pushes the screw out of the screwdriver. The tool 879 can, for example, be about 7 cm long, for tunneling, and can be embedded in a plastic tube as an inserter. As shown in FIG. 9, external pressure on the scalp using a finger can be used while the screw is penetrating the skull, and the plastic envelop can retract by folding.

Figure 10:
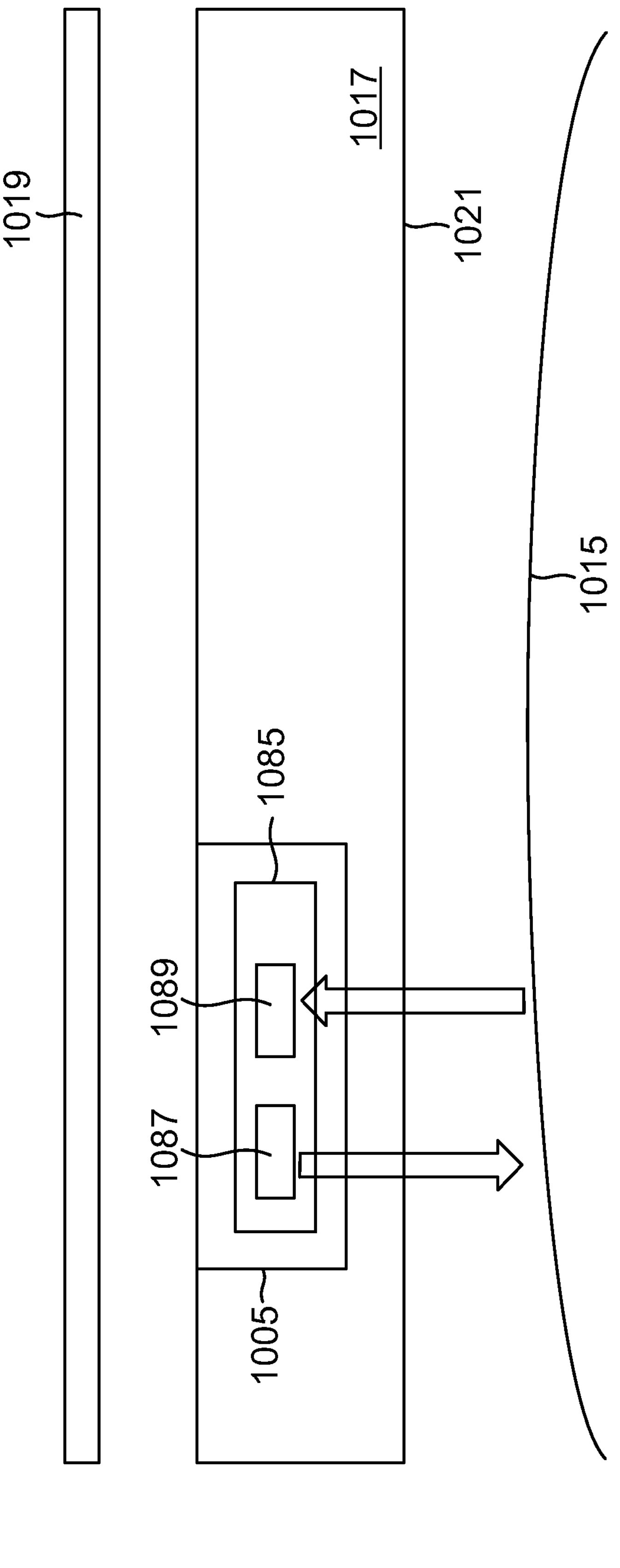
FIG. 10 is a schematic diagram illustrating an intra-osseous device, in accordance with an embodiment of the invention, that is configured to at least one of emit light signals to, and detect light signals from, the brain.

FIG. 10 is a schematic diagram illustrating an intra-osseous device 1005, in accordance with an embodiment of the invention, that is configured to at least one of emit light signals to, and detect light signals from, the brain 1015. As used herein, the term "light" refers generally to light in any suitable portion of the electromagnetic spectrum, including both light in the visible range of the electromagnetic spectrum and light in the near-infrared range of the electromagnetic spectrum. For example, the light can be visible light, such as light in the wavelength range between about 380 nm and about 750 nm wavelength; within the visible light range, the light can for example be red light, for example with a wavelength range between about 625 nm and about 750 nm wavelength; and the light can also be near-infrared light, such as light with a wavelength range of between about 750 nm and about 1400 nm wavelength; and the light can be from more than one of the foregoing ranges of wavelengths, and from any other suitable range of wavelengths of the electromagnetic spectrum. The emitted light signals can, for example, be near infrared or red signals emitted to the brain. The detected light signals can, for example, be near infrared signals scattered from the brain. The device comprises a light signal device 1085 configured to at least one of emit light signals to, and detect light signals from, a brain 1015. At least part of the body of the device includes at least one of a light emitter (such as a near infrared or red emitter) 1087 and a light detector (such as a near infrared detector) 1089 that extend within a bone of the skull 1017. The device has a size and a shape configured to be positioned wholly below a scalp 1019 and to extend at least partly within the bone of the skull 1017 without penetrating through to an interior 1021 of the bone of the skull. The light signal device 1085 can be one that only emits light signals, such as near infrared or red signals, to the brain; or can be one that only detects light signals, such as near infrared signals, from the brain; or the light signal device can be one that both emits light signals to, and detects light signals from, the brain. In one example, the light signal device 1085 can be a functional near infrared spectroscopy device. Such a device can be implemented by having the light signal device 1085 of a single intra-osseous device 1005 both emit and detect near infrared signals for use in the functional near infrared spectroscopy. Alternatively, one device 1005 can emit near infrared signals while a different device 1005, installed elsewhere in the skull, detects near infrared signals, for use in the functional near infrared spectroscopy. Such spectroscopy can, for example, be used to perform hemodynamic imaging of the brain. In another embodiment, the intra-osseous device 1005 can be a photobiomodulation device, which can emit light signals, such as near infrared or red signals, into the brain to perform photobiomodulation. The photobiomodulation device can, for example, be a photobiomodulation device configured to treat at least one of a neurological disorder and a neurodegenerative disorder. In one example, using near infrared pulses of about 810 nm wavelength, the photobiomodulation can be used to treat Alzheimer's Disease, although other treatments can be performed. Other features of the device 1005 can be similar to those illustrated for electrodes taught herein. For example, the device 1005 can be similarly coupled to a sub-scalp cable using an electrical attachment feature; can communicate using a wireless communications device; can communicate with a data storage unit positioned within a body; can have a similar size and shape, such as a diameter of the device of between about 0.5 millimeters and about 5 millimeters, and a height of the device of between about 2 millimeters and about 6 millimeters; can include a threaded feature configured to secure the device within the bone of the skull, or a peg configured to extend within the bone of the skull. As with other devices taught herein, as in FIG. 5, the size and shape of the device 1005 can be configured to permit the device to fit entirely within the bone of the skull, or the size and shape may comprise a portion of the device configured to extend above a top surface of the bone of the skull, while remaining wholly underneath the scalp.

A variety of different possible advantages can be achieved using embodiments taught herein. As one example, the craniode uses a recording plane that is within the bone of the skull, which can provide an advantageous tradeoff: it offers a signal-to-noise ratio far better than scalp or sub-scalp EEG, while not penetrating the internal cavity of the skull reduces its surgical and post-operative hemorrhagic and infectious risks.

In addition, the attachment mechanism of the craniode can, for example, allow it to be attached to sub-scalp cables. In that way, the craniode can be connected in an unobtrusive manner either to a fully implantable recorder, such as a device similar in physical form to a cochlear implant; or, for example, to an implantable hub/connector that is used to aggregate all cables from deployed craniodes, which are then routed through a single percutaneous connection to an external recorder.

In another example, the craniode can be attachable to contacts of subcutaneous EEG leads, thus enabling dual use of such leads: for recording sub-scalp EEG or as cables for recording intraosteal EEG from craniodes.

Also, with advancing active electrode technology, the craniodes can act as many independent units recording and transmitting EEG signals wirelessly for long-term storage.

In addition, if many craniodes are used, brain coverage can be as high as with scalp EEG, as all accessible recording sites on the skin can have an osseous counterpart a few millimeters beneath.

REFERENCES (1) Ross et al. 1993. A percutaneous epidural screw electrode for intracranial electroencephalogram recordings. Neurosurgery 33(2):332-4;

(2) Barnett et al. 1990. Epidural peg electrodes for the presurgical evaluation of intractable epilepsy. Neurosurgery 27(1):113-5.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. An intra-osseous device comprising a surgical metal bone screw, the intra-osseous device configured to at least one of sense electrical signals from a brain and electrically stimulate the brain, the device comprising:

an electrical conductor comprising an electrical contact surface configured to at least one of sense electrical signals from the brain and electrically stimulate the brain;

an electrical attachment feature configured to electrically connect the electrical conductor to a sub-scalp cable;

at least a portion of a body of the device, comprising the electrical conductor, being configured to extend within a bone of a skull; and the device comprising a size and a shape configured to be positioned wholly below a scalp and to extend at least partly within the bone of the skull without penetrating through the bone of the skull;

the electrical conductor comprises a top portion, a bottom portion and a shaft portion extending between the top and bottom portions, the bottom portion defining the electrical contact surface;

an electrically insulating material clad about the top portion and the shaft portion of the electrical conductor;

the top portion of the electrical conductor configured to be positioned wholly below the scalp, said top portion configured to be electrically coupled to the sub-scalp cable;

the shaft portion and the bottom portion of the electrical conductor configured to be positioned into a hole extending into the bone of the skull, such that the electrical contact surface is positioned within the bone of the skull to sense brain activity from an intra-osseous space; and wherein the top portion of the electrical conductor is a head with cross-drive grooves, the shaft portion of the electrical conductor is threaded and is coated with the electrically insulating material, and the bottom portion is an uninsulated tip defining the electrical contact surface;

wherein the cross-drive head is coated with the electrically insulating material except for an inner surface of the cross-drive grooves, and wherein the cross-drive grooves are adapted to receive an electrical contact portion of the sub-scalp cable.

2. The intra-osseous device of claim 1, wherein the device functions as at least one of an electrical brain activity recording electrode and an electrical brain stimulation electrode.

3. The intra-osseous device of claim 1, the device being electrically coupled to the sub-scalp cable.

4. The intra-osseous device of claim 1, comprising a wireless communications device configured to at least one of transmit and receive wireless signals.

5. The intra-osseous device of claim 1, wherein the size and shape comprises at least one of a diameter of the device of between 0.5 millimeters and 5 millimeters, and a height of the device of between 2 millimeters and 6 millimeters.

6. The intra-osseous device of claim 1, wherein the portion of the body of the device comprises either a threaded feature configured to secure the device within the bone of the skull, or a peg configured to extend within the bone of the skull.

7. The intra-osseous device of claim 1 further comprising an isolating and protective cap adapted to mate with the cross-drive grooves not occupied by the sub-scalp cable to retain and isolate the sub-scalp cable therebetween.

8. The intra-osseous device of claim 1, comprising the electrical attachment feature configured to electrically connect the electrical conductor to the sub-scalp cable, the electrical attachment feature comprising an elastic flap under which a portion of the sub-scalp cable can be inserted to make electrical connection with the electrical conductor.

* * * * *